United States Patent [19]
Ikeda et al.

[11] 4,416,813
[45] Nov. 22, 1983

[54] ARTIFICIAL CARRIER FOR IMMOBILIZATION OF BIOLOGICAL PROTEINS

[75] Inventors: Mikio Ikeda, Tachikawa; Takayuki Tomizawa, Tokyo, both of Japan

[73] Assignee: Fujizoki Pharmaceutical Co. Ltd., Tokyo, Japan

[21] Appl. No.: 359,249

[22] Filed: Mar. 18, 1982

[30] Foreign Application Priority Data

Mar. 18, 1981 [JP] Japan .................................. 56-37855
Mar. 31, 1981 [JP] Japan .................................. 56-46211

[51] Int. Cl.$^3$ ...................... C09H 7/00; C12N 11/02; C12N 11/10; G01N 33/54
[52] U.S. Cl. ........................................ 260/117; 435/7; 435/174; 435/177; 435/178; 435/179; 436/528
[58] Field of Search ............... 435/174, 177, 178, 179, 435/181, 7; 252/316, 425.3, 426, 428; 424/12, 94; 260/117; 436/528

[56] References Cited

U.S. PATENT DOCUMENTS

| 3,639,558 | 2/1972 | Csizmas et al. | 424/12 |
| 3,697,437 | 10/1972 | Fogle et al. | 260/117 X |
| 3,717,469 | 2/1973 | Slonimsky et al. | 260/117 X |
| 3,838,007 | 9/1974 | von Velzen | 435/177 X |
| 4,216,108 | 8/1980 | Sels et al. | 260/117 X |

Primary Examiner—David M. Naff
Attorney, Agent, or Firm—Burgess, Ryan & Wayne

[57] ABSTRACT

A novel artificial carrier is disclosed which is prepared from gelatin, a water-soluble polysaccharide, a sodium metaphosphate and an aldehyde. The carrier can be used to immobilize antibodies, antigens or enzymes. Immobilized antigens and antibodies can be used as a diagnostic reagent in assays involving antigen-antibody reactions.

23 Claims, No Drawings

ARTIFICIAL CARRIER FOR IMMOBILIZATION OF BIOLOGICAL PROTEINS

BACKGROUND OF THE INVENTION

The present invention relates to a novel carrier which may be sensitized with antigen and antibody and is capable of immobilizing enzyme. A method of preparing the carrier is also disclosed.

In the field of serological tests, indirect passive hemagglutination using an antigen-antibody reaction is widely employed to diagnose various diseases. This reaction is based on the fact that the antigen or antibody which is fixed on the surface of carrier particles reacts with the corresponding antigen or antibody in a sample serum. As a result, agglutination of the particle takes place.

Non-biological particles, such as polystyrene latex, kaolin and carbon powder and biological particles, such as mammalian erythrocytes and microbial cells may be used as carriers in the serological tests described above. Generally, non-biological particles are chemically stable, and are not antigenic. However, antigen and antibody are not tightly adsorbed on the non-biological carrier. For example, when the carrier having antigen or antibody absorbed thereon (sensitized carrier), is lyophilized in order to preserve it, the antigen or the antibody is released from the carrier particles. Consequently, the sensitized carrier should be preserved in the form of a suspension under low temperatures and in the absence of light. As a result, such sensitized carriers have a relatively short shelf life.

Kaolin and carbon powder suffer from the disadvantage in that it is difficult to obtain particles of equal size. Polystyrene latex is deficient because it tends to aggregate naturally in the neutral pH range where indirect passive agglutination is usually carried out.

On the other hand, mammalian erythrocytes and microbial cells are biological particles which have substantially uniform sizes. However, their size depends on the species of animal or microorganism, and accordingly, it is not always possible to obtain particles having the desired size. Among the biological carriers, mammalian erythrocytes are the most readily available and their sizes are uniform. However, their surfaces have specific antigenicity which can lead to nonspecific agglutination. Furthermore, it is difficult to obtain high quality erythrocytes due to variations of the biological, chemical and physical properties of the mammals from which the erythrocytes are obtained.

It has now been found that when the particles of gelatin, produced from a gelatin solution within a particular pH range containing a water-soluble polysaccharide and a sodium metaphosphate, are insolubilized with a cross-linking agent such as an aldehyde, the particles are suitable as a carrier for antigens and antibodies for indirect passive agglutination.

Any commercial gelatin material may be used in the invention. Among the most preferred commercial gelatin products are gelatins having an isoelectric point at a pH between about 8 and 9.

The water-soluble polysaccharide is used as a viscosity increasing agent or a paste, and includes derivatives and salts of such polysaccharides. Examples of such polysaccharides are arabic gum, carboxymethyl cellulose, sodium alginate, agar, and so on.

The sodium metaphosphate used in the invention is a compound having the formula of $(NaPO_3)_n$, where n is a whole number from 3 to 6, and includes sodium trimetaphosphate and sodium hexametaphosphate.

The solution may also contain such other components as a water-miscible organic solvent, a nonionic or anionic surfactant, and a coloring agent.

The water-miscible organic solvent may optionally be added to accelerate the precipitation of the gelatin particles. Such solvents include lower alcohols, such as methanol, ethanol and isopropanol, and acetone. Since the organic solvent gives hydrophobicity to the particles, their physical and chemical properties differ somewhat from the particles which are made without the solvent.

The anionic surfactant and the nonionic surfactant may optionally be employed in order to prevent aggregation of the particles formed in the solution. The anionic surfactant includes alkylsulfosuccinic acids, alkylsulfomaleic acids, alkylsulfuric acid esters, and polyoxyethylene alkyl ether sulfuric acid esters. The nonionic surfactant includes polyoxyethylene fatty acid esters, polyoxyethylene alkyl ethers, polyoxyethylene alkyl phenyl ethers, and polyethylene glycol fatty acid esters wherein the alkyl group for both groups of surfactants has between 6 and 25 carbon atoms. Aggregation of the particles may also be prevented by chilling the solution below 10° C. as soon as the particles form.

If it is desirable to color the carrier particles, a suitable coloring agent may be added to the solution. Alternatively, the insolubilized particles described below may be treated with the coloring agent. However, in the former case, the coloring agent is concentrated on the particles formed in the solution, thereby reducing the amount of the coloring agent needed. Moreover, the coloring agent is uniformly distributed to the inner part of the particles, and accordingly, the particles are tightly colored.

The coloring agents include red coloring matter, such as rhodamine, rose bengal, ponceau 3R, Bordeaux S, fuchsin, eosine, and neutral red, and blue coloring matter, such as crystal violet, toluidine blue, and methylene blue. However, reactive dyes, such as reactive red and reactive blue are most preferable, because the color of the carrier does not come off.

The concentration of the components in the solution are discussed below. All percentages are percentages by weight unless otherwise noted. The concentration of gelatin in the solution is about 0.01 to 2%, preferably about 0.05 to 1.0%, the concentration of the water-soluble polysaccharide is about 0.01 to 2%, preferably about 0.05 to 1.0%, and the concentration of sodium metaphosphate is about 3 to 15% by dry weight of the gelatin. The amount of the optional components may vary. The preferred concentration of the water-miscible organic solvent is about 4 to 25 vol%. The preferred concentration of the anionic surfactant is about 0.001 to 0.01%, and that of the nonionic surfactant is about 0.01 to 0.1%. The concentration of the coloring agent is usually about 0.005 to 0.5%.

The process of preparing the solution is not limited, and for example, each component may be separately dissolved in warm water and then the resulting solutions are mixed. Alternatively, all components may be placed in a vessel and then dissolved. However, it is preferable that the water-miscible organic solvent is added as one of the last components to make a suitable dispersion of the other components. Further, it is preferable to separately dissolve the water-soluble polysaccharide because the water-soluble polysaccharide often contains a small amount of insoluble components.

If the pH of the solution is lower than the isoelectric point, white turbidity results when the gelatin is reacted with the water-soluble polysaccharide. Since this white turbidity is undesirable, the turbidity must be removed by the addition of alkali prior to the pH adjustment described below. Accordingly, when gelatin having an isoelectric point at a pH of about 8 to 9 is employed, alkali is preferably added to the solution until the pH of the solution reaches within a range around the isoelectric point.

The temperature of the solution should be higher than the temperature of gelation of the gelatin. The temperature of gelation depends on the concentration of the gelatin, etc., and it is usually between about 25° and 50° C.

Subsequently, the pH of the solution is adjusted to 2.5 to 6.0 by adding acid while the solution is stirred. During the pH adjustment, particles are produced in the solution. In order to produce uniform particles, the acid is added dropwise to the solution, while the solution is heated at between about 35° and 50° C. under moderate stirring. The optimal pH within the range of pH 2.5 to 6.0 depends on the desired size of particles and composition of the solution. For example, when the particles are employed as the carrier for indirect passive agglutination, the suitable size of the carrier is between about 2 and 10 microns, and in this case, the optimal pH is in the range of 4.0 to 5.5. The acid employed for the pH adjustment is not limited, and either an inorganic acid or organic acid may be employed. However, a weak acid, such as acetic acid, is preferred.

There is no equilibrium relation between the particles formed by the pH adjustment and the mother liquor, because the particles do not disappear when the temperature of the solution is lowered below the temperature of gelation. The particles are usually positively charged, through it depends on the ratio of gelatin to water-soluble polysaccharide. On the surface of the particles, metaphosphate ion is oriented and electric double layer is constructed around the particles. This electric double layer makes the suspension of the particles stable.

After the addition of the acid, the suspension of the particles is immediately cooled below 10° C. in order to prevent aggregation of the particles. Then, an aldehyde cross-linking agent is added to the suspension, and the particles are insolubilized by standing overnight at a temperature below 10° C. The amount of the cross-linking agent is between about 0.1 and 200% by dry weight of gelatin. The cross-linking agent is preferably glutaraldehyde, formaldehyde, glyoxal, crotonaldehyde, acrolein, and acetaldehyde. Glutaraldehyde is the most preferred.

After treatment with the cross-linking agent, the particles are recovered by means of centrifugation, etc., and washed twice or three times with water containing surfactant, if necessary. In this case, the same surfactant as employed for dispersing the particles may be used at the same concentration.

The insolubilized particles thus produced may be used as a carrier for various purposes. However, the particles sometimes swell in a salt solution, and accordingly, it is preferable that the particles are further treated with the aldehyde cross-linking agent. For example, when the carrier is sensitized with antigen in a phosphate buffer solution, the carrier is preferably treated with formalin under the same conditions as the case of erythrocytes. By treatment with formalin, swelling of the carrier is alleviated, and the carrier may be preserved for a long term because of the sterilizing effect of formalin.

The carrier of the invention can immobilize antigen, antibody, enzyme and so on. As to the method of immobilization, for example, when antigen or antibody is sensitized on the carrier, the sensitization may be carried out according to conventional sensitization procedures using mammalian erythrocytes as the carrier. Such immobilization methods include the method of using tannic acid, the method of using formalin, the method of using glutaraldehyde, the method of using bisdiazotized benzidine, the method of using pyruvic aldehyde, the method of using toluene-2, 4-diisocyanate, etc.

The capability of the carrier of the invention is almost equal to that of mammalian erythrocytes which are considered the best carrier for indirect passive agglutinaton. Moreover, the present carriers are superior to the mammalian erythrocytes, because they are chemically and physically uniform and stable, and have no antigenic activity. And, according to the method of the invention, the carrier having the desired size is easily and inexpensively produced on a large scale.

The present invention is further illustrated by the following examples which are not intended to limit the scope of the invention.

EXAMPLE 1

4 Grams of gelatin having an isoelectric point at a pH of 9 were dissolved in water at 40° C., and the volume of the solution was adjusted to 100 ml. The pH of the solution was then adjusted to 9. 4 Grams of arabic gum were dissolved in water, and the volume of the solution was adjusted to 100 ml. Insoluble matters were filtered out, and the filtrate was warmed to 40° C.

50 ml of the above gelatin solution and 50 ml of the above filtrate were mixed, and the mixture was poured into 300 ml of 30 vol% aqueous methanol which was previously warmed to 40° C., and the mixture was sufficiently stirred.

1.6 ml of 10% sodium hexametaphosphate solution, 2 ml of 1% alkylsulfomaleic acid (trade name: Demol Ep, manufactured by Kao Soap Co.) and 6 ml of a 1% reactive blue solution were added to the mixture, and the mixed solution was sufficiently stirred. Subsequently, 10 vol% of acetic acid was added dropwise to the mixed solution while it was kept at 40° C. The pH of the mixed solution was adjusted to 4.8 to obtain particles.

The suspension of the particles was cooled to 5° C. in an ice bath, and 1.3 g of glutaraldehyde were added to the suspension. After stirring, the suspension was allowed to stand at 5° C. overnight. Then, the suspension was centrifuged at 2000 rpm for 10 minutes, and the resulting insolubilized particles were collected. The particles were suspended in 0.005% Demol Ep solution, and then centrifuged again. The washing procedure was repeated three times, and the particles were suspended in 4 vol% of formalin. The suspension was then allowed to stand at 5° C. for one week.

The yield of the carrier particles was 7.7 g, and 75% of the particles were in the range of 3 to 6 microns.

Electrophoretic mobility of the particles were measured using Laser Zee system 3000 (manufactured by Pen Ken Inc., N.Y., U.S.A.). About 1 ml of the suspension of the particles was placed in a cylindrical cell of which the diameter was 1 mm and the length was 20 mm, and the mobility of the particles at 25° C. at the potential gradient of 1048 V/m was measured. The electrophoretic mobility thus obtained was −0.969 ±0.009 micron/sec/V/cm.

Uncolored particles were prepared in the same manner as the above colored particles except that reactive blue solution was not added. The electrophoretic mobility of the uncolored particles measured under the same conditions was −0.972 ±0.012 micron/sec/V/cm.

Since electrophoretic mobility of sheep erythrocytes is −1.08 micron/sec/V/cm, the mobilities of the above particles were nearly equal to the mobility of sheep erythrocytes.

Example of Use in TPHA Test

The carrier particles produced in accordance with Example 1 were suspended in a phosphate buffered saline (hereinafter referred to as PBS) of pH 7.2 containing tannic acid, the concentration of which is shown in Table 1, so that the concentration of the particles was 2.5%. The suspension was warmed at 37° C. for 15 minutes. The particles were collected by centrifuging, and washed sufficiently with saline solution.

Treponema pallidum (hereinafter referred to as TP), the causative agent of syphilius, was suspended in PBS at a pH of 6.4 and sonicated at 10 KHz output in an ice bath for 10 minutes. The sonicated TP was employed as a TP antigen.

The above particles treated with tannic acid solution were suspended in pH 6.4 PBS to obtain a concentration of 5%. The suspension was mixed with an equal volume of the TP antigen solution which was previously diluted (the dilution ratio is shown in Table 1). The mixture was warmed at 37° C. for 40 minutes, to thereby obtain TP antigen sensitized on the particles.

The particles sensitized with antigen were collected by centrifuging, and washed sufficiently with pH 6.4 PBS. The washed particles were then suspended in a disperse medium so that the concentration of the particles was 5%.

The suspension of the particles sensitized with antigen was reacted with a syphilis positive serum on a micro titer plate. The results are shown in Table 1.

TPHA (diagnostic reagent for syphilis, produced by Fujizoki Pharmaceutical Co., Ltd.) in which sheep erythrocytes were employed as a carrier was also carried out as a control experiment. The results are also shown in Table 1.

TABLE 1

| Carrier | Tannic Acid (ppm) | Dilution Ratio of Antigen | Dilution Ratio of Serum | | | | | |
|---|---|---|---|---|---|---|---|---|
| | | | 640 | 1280 | 2560 | 5120 | 10240 | 20480 |
| Carrier of the Invention | 1 | 40 | ++ | ++ | ++ | ++ | + | − |
| | 5 | | ++ | ++ | ++ | ++ | ++ | + |
| | 10 | | ++ | ++ | ++ | ++ | + | − |
| | 1 | 60 | ++ | ++ | ++ | + | − | − |
| | 5 | | ++ | ++ | ++ | ++ | + | − |
| | 10 | | ++ | ++ | ++ | + | − | − |
| | 1 | 80 | ++ | ++ | + | − | − | − |
| | 5 | | ++ | ++ | ++ | + | − | − |
| | 10 | | ++ | ++ | + | − | − | − |
| Sheep Cells | 10 | | ++ | ++ | ++ | ++ | + | − |

Immobilization of Enzyme

The carrier particles obtained in this Example were suspended in pH 7.2 PBS containing 10 ppm of tannic acid so that the concentration of the particles was 2.5%. The suspension was warmed at 37° C. for 15 minutes. The particles were collected by centrifuging, and washing sufficiently with saline solution. The washed particles were then suspended in pH 7.2 PBS so as to obtain a concentration of 1%.

Highly pure streptokinase was dissolved in pH 7.2 PBS to obtain a solution having a concentration of 128 U/ml.

4 ml of the suspension of the washed particles were mixed with 4 ml of the streptokinase solution, and the mixture was warmed at 37° C. for 30 minutes. The particles were collected by centrifuging, washed twice with pH 7.2 PBS, and suspended in the gelatin buffer havomg a pH of 7.2 so that the concentration of the particles was 1%. The above gelatin buffer contained 5 g/l of gelatin, 10 g/l of sodium chloride and 13.6 g/l of potassium dihydrogen phosphate.

Streptokinase activity of this suspension was about 16 U, and accordingly, about 12% of the enzyme in the solution was immobilized on the particles.

The streptokinase activity was determined as follows: 0.25 ml of the enzyme solution or the suspension of the particles was added with 0.1 ml of human plasma and 0.05 ml of thrombin solution, and warmed at 37° C. for 30 minutes. The enzyme activity is expressed as the maximum dilution capable of bringing fibrinolysis of coagulated plasma.

EXAMPLE 2

The carrier particles were prepared in the same manner as employed in Example 1, except that 30 vol% aqueous methanol was replaced by 30 vol% aqueous ethanol, 2 ml of 1% Demol Ep was replaced by 8 ml of 1 vol% polyoxyethylene phenyl ether (trade name: Emulgen A-60, manufactured by Kao Soap Co.), and the final pH was adjusted to 4.9 using acetic acid.

The yield of the carrier particles was 7.8 g, and 70% of the particles were in the range of 7 to 11 microns.

EXAMPLE 3

The carrier particles were prepared in the same manner as employed in Example 1, except for the following: 4 g of arabic gum were replaced by 1 g of carboxymethyl cellulose, and 30 vol% aqueous methanol was replaced by 30 vol% aqueous ethanol. The amount of gelatin, 10% sodium hexametaphosphate solution, 1% Demol Ep solution, 1% reactive blue solution, and glutaraldehyde was one-fourth of that described in Example 1. The final pH using acetic acid was 4.6.

The yield of the carrier particles was 3.8 g, and 90% of the particles were in the range of 1 to 2 microns.

EXAMPLE 4

The carrier particles were prepared in the same manner as employed in Example 1, except for the following:

The volume of the gelatin solution was 40 ml, and the volume of the arabic gum solution was 60 ml. The volume of the 10% sodium hexametaphosphate solution was 1.2 ml, the volume of the 1% reactive blue solution was 4.8 ml, and the weight of glutaraldehyde was 1.0 g. The final pH using acetic acid was 4.6.

The yield of the carrier particles was 6.4 g, and 90% of the particles were in the range of 1 to 2 microns.

Electrophoretic mobility of the particles measured in the same manner as Example 1 was −0.939 ±0.059 micron/sec/V/cm.

EXAMPLE 5

The carrier particles were prepared in the same manner as employed in Example 1, except for the following:

The volume of the gelatin solution was 60 ml, and the volume of the arabic gum solution was 40 ml. The volume of the 10% sodium hexametaphosphate solution was 2 ml, the volume of the 1% reactive blue solution was 7.2 ml, and the weight of glutaraldehyde was 1.8 g. The final pH using acetic acid was 4.8.

The yield of the carrier particles was 8.6 g, and 75% of the particles were in the range of 3 to 6 microns.

Electrophoretic mobility of the particles measured in the same manner as Example 1 was −0.996 ±0.040 micron/sec/V/cm.

EXAMPLE 6

15 Grams of the gelatin having an isoelectric point of pH 9 was dissolved in 485 g of water at 40° C., and the pH of the gelatin solution was adjusted to 9 using 10% sodium hydroxide.

15 Grams of arabic gum were dissolved in 485 g of water, the insoluble residue was filtered out, and the filtrate was warmed to 40° C.

60 Parts by volume of the gelatin solution were mixed with 40 parts by volume of the above filtrate, and 750 g of the mixture were poured into 2250 ml of 30 vol% aqueous ethanol which was previously warmed to 40° C. The mixture was then stirred sufficiently.

12 Grams of 10% sodium hexametaphosphate solution were added to the mixture, and then 10 vol% acetic acid was added dropwise to the mixed solution until the pH of the mixed solution reached 4.9. Particles were formed by the pH adjustment.

Subsequently, 7.5 g of Emulgen A-60 were added little by little to the suspension of the particles, and the suspension was stirred well. The suspension was cooled to room temperature, and 0.2 g of glutaraldehyde was then added. The suspension was then stirred for about 1 hour, and allowed to stand overnight. The resulting insolubilized particles were collected by centrifuging at 2000 rpm for 5 minutes. The particles were suspended in 0.2 vol% of the above surfactant solution, and then centrifuged again. The washing procedure was repeated twice, and the washed particles were immersed in 0.05% rose bengal solution overnight. The red particles were suspended in 8% formalin, and allowed to stand at 4° C. overnight.

The carrier particles were almost uniform, and the size of most of the particles was about 10 microns.

The carrier particles were treated with tannic acid and sensitized with TP antigen, according to the same manner as employed in the previous "Example of Use in TPHA Test".

The particles sensitized with TP antigen were reacted with syphilis positive serum on a micro titer plate, and the results are shown in Table 2.

TPHA (the product of Fujizoki Pharmaceutical Co., Ltd.) wherein sheep erythrocytes were employed as a carrier was also carried out as a control experiment. The results are also shown in Table 2.

TABLE 2

| Carrier | Dilution Ratio of Serum | | | | | | | |
|---|---|---|---|---|---|---|---|---|
| | 80 | 160 | 320 | 640 | 1280 | 2560 | 5120 | 10240 |
| The Invention | ++ | ++ | ++ | ++ | ++ | ++ | + | − |
| Sheep Cells | ++ | ++ | ++ | ++ | ++ | ++ | + | − |

EXAMPLE 7

10 Grams of gelatin having an isoelectric point of pH 9 were dissolved in 490 g of water at 40° C., and the pH of the gelatin solution was adjusted to 9 using 10% sodium hydroxide.

10 Grams of arabic gum were dissolved in 490 g of water, the insoluble residue was filtered out, and the filtrate was warmed to 40° C.

The above gelatin solution was mixed with an equal volume of the above filtrate, and 750 g of the mixture were poured into 2250 g of 20 vol% aqueous ethanol which was previously warmed to 40° C. 6 Grams of 10% sodium metaphosphate were added to the above mixture while it was stirred at 40° C. Subsequently, 10 vol% of acetic acid was added dropwise to the mixed solution until the pH was 4.6. Particles were formed by the pH adjustment.

1.5 Grams of Demol Ep were gradually added to the suspension of the particles, and then the particles were insolubilized according to the method of Example 6, and colored red using 0.2% Bordeaux S solution.

The size of most of the carrier particles was about 5 microns.

EXAMPLE 8

15 Grams of the gelatin having an isoelectric point of pH 9 were dissolved in 235 g of water at 40° C., and the gelatin solution was adjusted to pH 9 using 10% sodium hydroxide.

15 Grams of arabic gum were dissolved in 235 g of water, the insoluble residue was filtered out, and the filtrate was warmed to 40° C.

The gelatin solution was mixed with the above filtrate, and the mixture was poured into 1500 g of 20 vol% n-propanol which was previously warmed to 40° C. 1.2 Grams of sodium hexametaphosphate were dissolved in the mixture, and stirred well. Subsequently, 10 vol% of acetic acid was added dropwise to the mixed solution until the pH was 4.6. Particles having a size of about 10 microns were formed by the pH adjustment. According to the method of Example 6, the particles were suspended using the surfactant, insolubilized using 0.2 g of glutaraldehyde, and collected by centrifuging.

EXAMPLE 9

Using acetone instead of n-propanol, the carrier particles were obtained according to the method of Example 8. In this case, the final pH was adjusted to 4.7 using acetic acid and the size of most of the particles was about 15 microns.

EXAMPLE 10

4 Grams of the gelatin having an isoelectric point of pH 9 were dissolved in water at 40° C. to a concentration of 4 g/dl, and the gelatin solution was adjusted to pH 9 using 10% sodium hydroxide.

4 Grams of arabic gum were dissolved in water to a concentration of 4 g/dl, the insoluble residue was filtered out, and the filtrate was warmed to 40° C.

50 ml of the gelatin solution were mixed with 50 ml of the above filtrate, and 300 ml of 30 vol% aqueous ethanol, 1.6 ml of 10% sodium hexametaphosphate, and 6 ml of 1% reactive red solution were added to the mixture. Then, the mixed solution was stirred well, and warmed to 40° C. Subsequently, 10 vol% acetic acid was added dropwise to the mixed solution with stirring until the pH was 5.0. Particles were formed by the pH adjustment.

The suspension of the particles was immediately cooled to 5° C. in an ice bath, and 1.3 g of glutaraldehyde were added. The suspension was stirred well, and allowed to stand overnight at 5° C. The suspension was then centrifuged at 2000 rpm for 10 minutes, and the particles were collected. The collected particles were suspended in 0.01% Demol Ep solution, and centrifuged again. The washing procedure was repeated three times. The washed particles were suspended in 4 vol% formalin, and allowed to stand at 5° C. for one week.

The yield of the carrier particles was 6.4 g, and 75% of the particles were in the range of 3 to 6 microns.

EXAMPLE 11

5 Grams of the gelatin having an isoelectric point of pH 9 were dissolved in 500 g of water at 40° C., and the gelatin solution was adjusted to pH 9 using 10% sodium hydroxide.

5 Grams of arabic gum were dissolved in 500 g of water, the insoluble residue was filtered out, and the filtrate was warmed to 40° C.

The gelatin solution was mixed with the filtrate, and 4 ml of 10% sodium hexametaphosphate. Subsequently, 10 vol% acetic acid solution was added dropwise to the mixed solution with stirring until the pH was 4.6. Particles were formed by the pH adjustment.

2.5 Grams of polyoxyethylene sorbitan fatty acid ester (trade name: Nikkol T0-10M, manufactured by Nikko Chemicals Co.) were added to the suspension of the particles and stirred well. The suspension was cooled to room temperature, and 0.1 g of glutaraldehyde was added to the suspension. The suspension was stirred for one hour, and allowed to stand overnight. The particles were collected by centrifuging at 2000 rpm for 10 minutes. The collected particles were suspended in 0.2 vol% of the above surfactant, and collected by centrifuging again. The washing procedure was repeated three times, and the washed particles were immersed overnight in 0.05% rose bengal solution. The red colored beads were suspended in 4% formalin, and allowed to stand for one week at 4° C.

The yield of the carrier particles was 18 g, and the size of most of the particles was about 5 microns and almost uniform.

EXAMPLE 12

Varying the concentrations of gelatin and arabic gum, the carrier particles were produced according to the method of Example 11. The results are shown in Table 3. In these experiments, when the concentrations of gelatin and arabic gum were higher than 0.6%, the size of the particles suddenly became larger and the degree of uniformity decreased. When the gelatin concentration was higher than 0.9%, the particles formed were immediately aggregated to a high degree.

TABLE 3

| Concentration of gelatin and arabic gem (%) | Sodium hexametaphosphate (g) | Final pH | Yield (g) | Size ($\mu$) |
|---|---|---|---|---|
| 0.05 | 0.04 | 3.6 | 9.0 | 5 |
| 0.1 | 0.08 | 3.8 | 12 | 5 |
| 0.25 | 0.20 | 4.1 | 15 | 5 |
| 0.4 | 0.32 | 4.5 | 17 | 5 |
| 0.5 | 0.40 | 4.6 | 17 | 5 |
| 0.6 | 0.48 | 4.7 | 18 | 20 |

EXAMPLE 13

4 Grams of gelatin having an isoelectric point of pH 9 were dissolved in water at 40° C. to a concentration of 4 g/dl, and the gelatin solution was adjusted to pH 9 using 10% sodium hydroxide.

4 Grams of arabic gum were dissolved in water to a concentration of 4 g/dl, the insoluble residue was filtered out, and the filtrate was warmed to 40° C.

50 ml of the gelatin solution were mixed with 50 ml of the filtrate, and the mixture was diluted with 300 ml of distilled water at 40° C. 1.6 ml of 10% sodium hexametaphosphate, 8 ml of 1 vol% of Emulgen A-60 solution, and 6 ml of 1% reactive blue solution were added to the diluted mixture.

Subsequently, 10 vol% acetic acid was added to the mixed solution while it was maintained at 40° C. with stirring. The addition of the acetic acid was stopped when the pH of the solution reached 4.8. Particles were formed by the pH adjustment.

The suspension of the particles was cooled to 5° C. in an ice bath, and 1.3 g of glutaraldehyde were added to the suspension. The suspension was then stirred well, and allowed to stand overnight at the same temperature. The suspension was centrifuged at 2000 rpm for 10 minutes, and the particles were collected. The collected particles were suspended in 0.02 vol% Emulgen A-60 solution, and centrifuged again. The washing procedure was repeated three times. The washed particles were suspended in 4 vol% formalin, and allowed to stand at 5° C. for one week.

The yield of the carrier particles was 6.2 g, and 75% of the particles were in the range of 3 to 6 microns.

EXAMPLE 14

The carrier particles were prepared in the same manner as the method of Example 13, except that the Emulgen A-60 solution was not added to the diluted mixture.

In this case, the yield of the carrier particles was 7.5 g, and 75% of the particles were in the range of 2 to 3.2 microns.

What is claimed is:

1. A process for producing an artificial carrier for immobilization of biological proteins which comprises: forming a solution of gelatin, a water soluble polysaccharide and sodium metaphosphate having the formula $(NaPO_3)_n$, wherein n is a whole number from 3 to 6 at a temperature above the gelation temperature of said gelatin; mixing with agitation an acid with said solution to adjust the pH of said solution to between about 2.5 and 6 whereby particles are formed and treating said particles with an aldehyde to thereby insolubilize said particles.

2. The process of claim 1, wherein the concentration of gelatin is between about 0.01 and 2% by weight of said solution.

3. The process of claim 1, wherein said gelatin has an isoelectric point at a pH value of between about 8 and 9.

4. The process of claim 1, wherein said water-soluble polysaccharide is present in an amount between about 0.01 and 2% by weight.

5. The process of claim 4, wherein said water-soluble polysaccharide is selected from the group consisting of arabic gum, carboxymethyl cellulose, sodium alginate, and agar.

6. The process of claim 1, wherein said sodium metaphosphate is selected from the group consisting of sodium trimetaphosphate and sodium hexametaphosphate.

7. The process of claim 1, wherein said reaction temperature is between about 25° and 50° C.

8. The process of claim 7, wherein said temperature is between about 35° and 50° C.

9. The process of claim 1, further comprising adjusting the pH of said solution to between about 4.0 and 5.5.

10. The process of claim 1 or 9, further comprising adjusting the pH with a weak acid.

11. The process of claim 1, further comprising adding a water-miscible solvent to said solution.

12. The process of claim 11, wherein said water-miscible solvent is selected from the group consisting of lower alcohols and acetone.

13. The process of claim 1, further comprising dissolving said water-soluble polysaccharide in a first solution and adding said first solution to a second solution comprising said gelatin and said sodium metaphosphate.

14. The process of claim 1, wherein said aldehyde is selected from the group consisting of glutaraldehyde, formaldehyde, glyoxal, crotonaldehyde, acrolein and acetoaldehyde.

15. The process of claim 14, wherein said aldehyde is glutaraldehyde.

16. The process of claim 14 or 15, wherein the amount of said aldehyde is between about 0.1 and 200% by dry weight of said gelatin.

17. The process of claim 1 further comprising cooling said solution to a temperature below 10° C. after the pH of the solution has been adjusted to between about 2.5 and 6.

18. The process of claim 1, further comprising adding an anionic surfactant to said solution.

19. The process of claim 18, wherein said anionic surfactant is selected from the group consisting of alkylsulfosuccinic acids, alkylsulfomaleic acids, alkylsulfuric acid esters, and polyoxyethylene alkyl ether sulfuric acid esters.

20. The process of claim 1, further comprising adding a nonionic surfactant to said solution.

21. The process of claim 20, wherein said nonionic surfactant is selected from the group consisting of polyoxyethylene fatty acid esters, polyoxyethylene alkyl ethers, polyoxyethylene alkyl phenyl esters, and polyethylene glycol fatty acid esters.

22. The process of claim 1, further comprising adding a coloring agent to said solution.

23. The product produced by the process of claim 1.

* * * * *